United States Patent [19]

Shroot et al.

[11] Patent Number: 4,826,996
[45] Date of Patent: May 2, 1989

[54] 1,8,-DIHYDROXY-9-ANTHRONES SUBSTITUTED IN THE 10-POSITION

[75] Inventors: Braham Shroot, Antibes; Jean Maignan, Tremblay Les Gonesse; Gérard Lang, Epinay-Sur-Seine, all of France

[73] Assignee: Groupement d'Interet Economique dit Centre International De Recherches Dermatologioues C.I.R.D., France

[21] Appl. No.: 806,680

[22] Filed: Dec. 9, 1985

Related U.S. Application Data

[60] Division of Ser. No. 393,646, Jun. 29, 1982, Pat. No. 4,568,743, Continuation-in-part of Ser. No. 312,671, Oct. 19, 1981, abandoned.

[30] Foreign Application Priority Data

Oct. 21, 1980 [FR] France .................. 80 22454

[51] Int. Cl.$^4$ ......................... C07D 207/404
[52] U.S. Cl. .................... 548/529; 260/351; 544/173; 544/380; 546/225; 548/538; 548/545; 558/427; 560/56; 564/169; 564/152
[58] Field of Search .............. 548/548, 545, 528, 529, 548/538; 514/895; 564/169, 152; 560/56; 546/225

[56] References Cited

U.S. PATENT DOCUMENTS

| | | | |
|---|---|---|---|
| 1,837,326 | 12/1931 | Kranzlein et al. | 260/351 |
| 3,706,768 | 12/1972 | Bags | 598/252 X |
| 3,883,661 | 5/1975 | Young | 514/859 X |
| 3,984,534 | 10/1976 | Peel et al. | 514/381 |
| 4,007,271 | 2/1977 | Robertson | 424/234 |
| 4,055,659 | 10/1977 | Gander et al. | 549/441 |
| 4,190,594 | 2/1980 | Gander et al. | 424/59 |
| 4,299,846 | 11/1981 | Mustakallio et al. | 424/331 |
| 4,327,114 | 4/1982 | Brickl et al. | 514/680 |
| 4,568,743 | 2/1986 | Shroot et al. | 548/528 |
| 4,696,941 | 9/1987 | Shroot et al. | 514/423 |

FOREIGN PATENT DOCUMENTS 0017420 10/1980 European Pat. Off. .
2140007 11/1984 United Kingdom .

OTHER PUBLICATIONS

Hofer et al., Chemical Abstracts, 77722s, vol. 81, p. 443, 1984.
Schultz et al., Chemical Abstracts, vol. 88, 88:10498g, 88:104985h; 88:104986j, p. 538, 1978.
Chemical Abstracts, vol. 13, (1919), pp. 1310–1313.
Archiv der Pharmazie, vol. 310 (1977), pp. 776–780.

Primary Examiner—David B. Springer
Attorney, Agent, or Firm—Wegner & Bretschneider

[57] ABSTRACT

The invention concerns 1,8-dihydroxy-9-anthrones substituted in the 10-position of the formula:

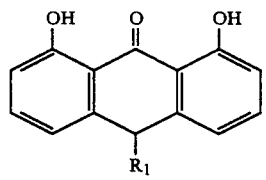

(I)

in which $R_1$ represents a group taken from the set constituted by:

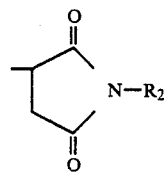

(a)

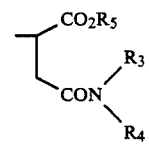

(c)

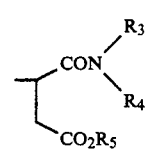

(b)

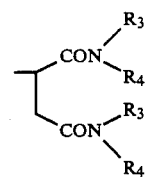

(d)

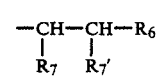

(e)

wherein $R_2$ represents H, $C_{1-8}$alkyl, $C_{1-3}$mono- or polyhydroxyalkyl, carbamoyl or phenyl, $R_3$, $R_4$, and $R_5$ represent H, $C_{1-8}$alkyl, $C_{3-8}$mono- or poly-hydroxyalkyl, possibly interrupted by an oxygen, $C_{3-6}$cycloalkyl, or $R_3$ and $R_4$ form a divalent group: $-(CH_2)_{(4\ or\ 5)}-$, $-(CH_2)_2-O-(CH_2)_2-$, or $-(CH_2)_2-N(R_8)-(CH_2)_2-$, $R_8$ being H, $-CH_3$, or $-CH_2CH_2OH$, $R_6$ represents $-CO_2R_5$, $-CN$, $CHO$, $-CONH_2$, or $-CONH-CH_2OH$, and $R_7$ and $R'_7$ are H or $-CH_3$, and their optical isomers.

Utilization of the compounds (I) in human or veterinary medicine, in particular in the treatment of psoriasis and of warts, in cosmetics.

5 Claims, No Drawings

1,8,-DIHYDROXY-9-ANTHRONES SUBSTITUTED IN THE 10-POSITION

This application is a divisional of Ser. No. 393,646, filed June 29, 1982 U.S. Pat. No. 4,768,743. This application is a continuation-in-part of U.S. patent application Ser. No. 312,671, filed Oct. 19, 1981, abandoned.

The present invention has as its object new chemical compounds belonging to 1,8-dihydroxy-9-anthrones substituted in the 10-position, as well as their use in human veterinary medicine, in particular in the treatment of psoriasis and of warts, and in cosmetics.

The 1,8-dihydroxy-9-anthrones substituted in the 10-position can be represented by the following general formula:

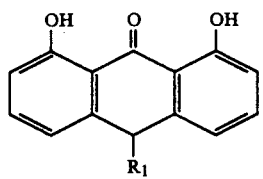

(I)

in which:

$R_1$ represents a group taken from the set constituted by:

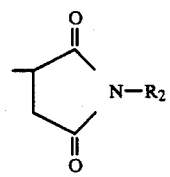

(a)

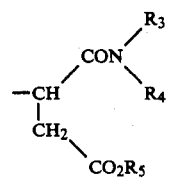

(b)

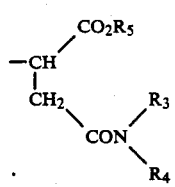

(c)

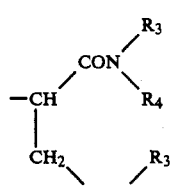

(d)

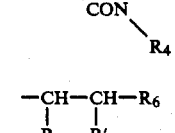
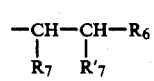

(e)

$R_2$ representing a hydrogen atom, a straight or branched chain alkyl group having 1-8 carbon atoms, a mono- or poly-hydroxyalkyl group, straight or branched chain, and having 1-3 carbon atoms, a carbamoyl group, or a phenyl group, $R_3$, $R_4$, and $R_5$ representing a hdyrogen atom, an alkyl group having 1-8 carbon atoms, a mono- or poly-hydroxyalkyl group, which may be interrupted by an oxygen atom and has 3-8 carbon atoms, or a cycloalkyl group having 3-6 carbon atoms, or $R_3$ and $R_4$, taken together, form a divalent group taken from the set constituted by:
—$(CH_2)_n$—, n being 4 or 5, —$(CH_2)_2$—O—$(CH_2)_2$—, and

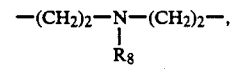

$R_8$ being a hydrogen atom, a methyl group, or a 2-hydroxyethyl group, $R_6$ representing —$CO_2R_5$, —CN, —CHO, —$CONH_2$, or —CONH—$CH_2OH$, and $R_7$ and $R'_7$ representing a hydrogen atom or a methyl group, and the optical isomers.

The compounds according to the invention can likewise exist in the form of salts when the group $R_1$ represents the group (b) and/or the group (c) in which $R_5$ represents a hydrogen atom.

In that case these salts correspond to the following general formulas:

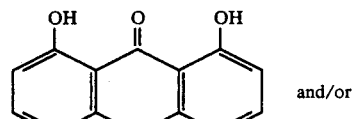

(IIb)

and/or

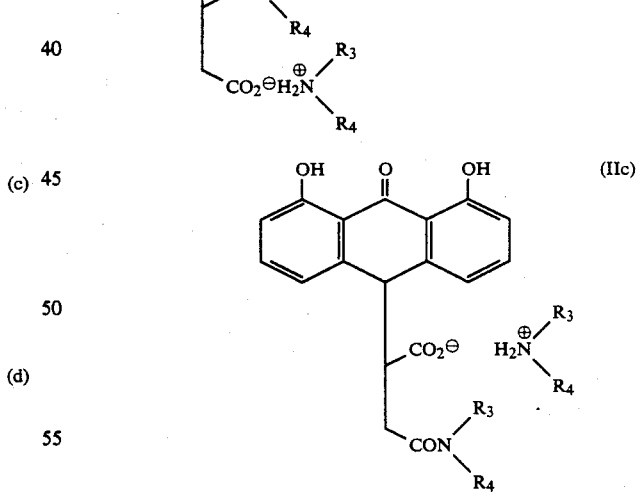

(IIc)

in which:

$R_3$ and $R_4$ have the same meanings as given above for formula (I).

Among the straight or branched chain alkyl groups with 1-8 carbon atoms as denoted in the groups $R_2$, $R_3$, $R_4$, and $R_5$, the following groups can in particular be cited: methyl, ethyl, propyl, isopropyl, butyl, isobutyl, tert. butyl, hexyl, and octyl.

Among the straight or branched chain mono- or poly-hydroxyalkyl groups, having 1-3 carbon atoms, the following can in particular be cited: hydroxymethyl, 2-hydroxyethyl, 2-hydroxypropyl, and 1,2-dihydroxypropyl.

Among the cycloalkyl groups as denoted by the group $R_3$ or $R_4$, the following groups can in particular be cited: cyclopropyl, cyclobutyl, cyclopentyl, and cyclohexyl.

By "lower alkyl group" according to the invention there is meant straight or branched chain groups having 1–4 carbon atoms such as methyl, ethyl, propyl, etc.

Among the compounds of formula I in which the group $R_1$ represents the group (a), there can be cited in particular those collected below in Table I.

TABLE I

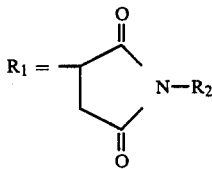

| Compound No. | | $R_2$ |
|---|---|---|
| 1 | 10-(1,8-dihydroxy-9-anthrone)-yl succinimide | H |
| 2 | 10-(1,8-dihydroxy-9-anthrone)-yl N—methyl succinimide | —CH$_3$ |
| 3 | 10-(1,8-dihydroxy-9-anthrone)-yl N—hydroxymethyl succinimide | —CH$_2$OH |
| 4 | 10-(1,8-dihydroxy-9-anthrone)-yl N—(2-hydroxyethyl) succinimide | —CH$_2$CH$_2$OH |
| 5 | 10-(1,8-dihydroxy-9-anthrone)-yl N—ethyl succinimide | —CH$_2$CH$_3$ |
| 6 | 10-(1,8-dihydroxy-9-anthrone)-yl N—(2,3-dihydroxypropyl) succinimide | —CH$_2$CHOH—CH$_2$OH |
| 7 | 10-(1,8-dihydroxy-9-anthrone)-yl N—(2-hydroxypropyl) succinimide | —CH$_2$CHOH—CH$_3$ |
| 8 | 10-(1,8-dihydroxy-9-anthrone)-yl N—carbamoyl succinimide | —CONH$_2$ |
| 9 | 10-(1,8-dihydroxy-9-anthrone)-yl N—phenyl succinimide | —C$_6$H$_5$ |

Among the compounds of formula I in which the group $R_1$ represents the group (c), there can be cited in particular those collected below in Table II.

TABLE II

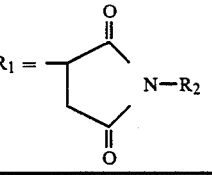

| Compound No. | | $R_7$ | $R'_7$ | $R_6$ |
|---|---|---|---|---|
| 10 | Ethyl 3-[10-(1,8-dihydroxy-9-anthrone)-yl]-propanoate | H | H | —CO$_2$C$_2$H$_5$ |
| 11 | 3-[10-(1,8-dihydroxy-9-anthrone)-yl]-propanoic acid | H | H | —CO$_2$H |
| 12 | 3-[10-(1,8-dihydroxy-9-anthrone)-yl]-propanal | H | H | —CHO |
| 13 | 3-[10-(1,8-dihydroxy-9-anthrone)-yl]-propionitrile | H | H | —CN |
| 14 | 3-[10-(1,8-dihydroxy-9-anthrone)-yl]-propionamide | H | H | —CONH$_2$ |
| 15 | Methyl 3-[10-(1,8-dihydroxy-9-anthrone)-yl] butanoate | —CH$_3$ | H | —CO$_2$CH$_3$ |
| 16 | Methyl 3-[10-(1,8-dihydroxy-9-anthrone)-yl]-2-methyl-propionate | H | —CH$_3$ | —CO$_2$CH$_3$ |
| 17 | 3-[10-(1,8-dihydroxy-9-anthrone)-yl] butanoic acid | —CH$_3$ | H | —CO$_2$H |
| 18 | 3-[10-(1,8-dihydroxy-9-anthrone)-yl]-2-methylpropionic acid | H | —CH$_3$ | —CO$_2$H |

Among the compounds of formula I in which the group $R_1$ represents the group (b) and/or (c), there can be cited in particular those collected below in Table III.

TABLE III

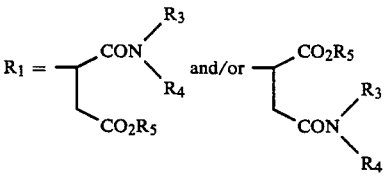

| Compound No. | (b) | (c) | $R_3$ | $R_4$ | $R_5$ |
|---|---|---|---|---|---|
| 19 | 10-(1,8-dihydroxy-9-anthrone)-yl succinamic acid | | H | H | H |
| 20 | 10-(1,8-dihydroxy-9-anthrone)-yl N—methyl succinamic acid | | H | —CH$_3$ | H |
| 21 | 10-(1,8-dihydroxy-9-anthrone)-yl N—ethyl succinamic acid | | H | —C$_2$H$_5$ | H |
| 22 | 10-(1,8-dihydroxy-9-anthrone)-yl N—propyl succinamic acid | | H | —n-C$_3$H$_7$ | H |
| 23 | 10-(1,8-dihydroxy-9-anthrone)-yl N—isopropyl succinamic acid | | H | —iso-C$_3$H$_7$ | H |
| 24 | 10-(1,8-dihydroxy-9-anthrone)-yl | | H | —n-C$_4$H$_9$ | H |

TABLE III-continued $$R_1 = \underset{CO_2R_5}{\overset{CON<R_3R_4}{\diagup}} \text{ and/or } \underset{CON<R_3R_4}{\overset{CO_2R_5}{\diagup}}$$

| Compound No. | (b) | (c) | R$_3$ | R$_4$ | R$_5$ |
|---|---|---|---|---|---|
| 25 | 10-(1,8-dihydroxy-9-anthrone)-yl N—cyclohexyl succinamic acid | | H | cyclohexyl | H |
| 26 | 10-(1,8-dihydroxy-9-anthrone)-yl N—octylsuccinamic acid | | H | —C$_8$H$_{17}$ | H |
| 27 | 10-(1,8-dihydroxy-9-anthrone)-yl N—(2-hydroxyethyl)-succinamic acid | | H | —CH$_2$—CH$_2$OH | H |
| 28 | 10-(1,8-dihydroxy-9-anthrone)-yl N—(2,3-dihydroxypropyl)-succinamic acid | | H | —CH$_2$—CHOH—CH$_2$OH | H |
| 29 | 10-(1,8-dihydroxy-9-anthrone)-yl morpholinosuccinamic acid | | —(CH$_2$)$_2$—O—(CH$_2$)$_2$— | | H |
| 30 | 10-(1,8-dihydroxy-9-anthrone)-yl pyrrolidinosuccinamic acid | | —(CH$_2$)$_4$— | | H |
| 31 | 10-(1,8-dihydroxy-9-anthrone)-yl piperidino-succinamic acid | | —(CH$_2$)$_5$— | | H |
| 32 | 10-(1,8-dihydroxy-9-anthrone)-yl dimethylsuccinamic acid | | —(CH$_2$)$_2$—N(CH$_3$)—(CH$_2$)$_2$— | | H |
| 33 | 10-(1,8-dihydroxy-9-anthrone)-yl 4-hydroxyethylpiperazino-succinamic acid | | —(CH$_2$)$_2$—N((CH$_2$)$_2$OH)—(CH$_2$)$_2$— | | |
| 34 | 10-(1,8-dihydroxy-9-anthrone)-yl N,N—dimethylsuccinamic acid | | —CH$_3$ | —CH$_3$ | H |
| 35 | 10-(1,8-dihydroxy-9-anthrone)-yl N,N—diethylsuccinamic acid | | —C$_2$H$_5$ | —C$_2$H$_5$ | H |
| 36 | 10-(1,8-dihydroxy-9-anthrone)-yl N,N—dipropylsuccinamic acid | | —nC$_3$H$_7$ | —nC$_3$H$_7$ | H |
| 37 | 10-(1,8-dihydroxy-9-anthrone)-yl N,N—di-n-butylsuccinamic acid | | —nC$_4$H$_9$ | —nC$_4$H$_9$ | H |
| 38 | 10-(1,8-dihydroxy-9-anthrone)-yl N,N—di-(2-hydroxyethyl)-succinamic acid | | —CH$_2$—CH$_2$OH | —CH$_2$—CH$_2$OH | H |
| 39 | 10-(1,8-dihydroxy-9-anthrone)-yl N—(2-hydroxyethyloxyethyl)-succinamic acid | | H | —(CH$_2$)$_2$—O—(CH$_2$)$_2$OH | H |
| 40 | Methyl 10-(1,8-dihydroxy-9-anthrone)-yl 3-carbamoylpropanoate | | H | H | —CH$_3$ |
| 41 | Methyl 10-(1,8-dihydroxy-9-anthrone)-yl 3-N—methylcarbamoyl-propanoate | | H | —CH$_3$ | —CH$_3$ |
| 42 | Methyl 10-(1,8-dihydroxy-9-anthrone)-yl 3-N—ethylcarbamoyl-propanoate | | H | —C$_2$H$_5$ | —CH$_3$ |
| 43 | Methyl 10-(1,8-dihydroxy-9-anthrone)-yl 3-N—propylcarbamoyl-propanoate | | H | —C$_3$H$_7$ | —CH$_3$ |
| 44 | Methyl 10-(1,8-dihydroxy-9-anthrone)-yl 3-N—butylcarbamoyl-propanoate | | H | —C$_4$H$_9$ | —CH$_3$ |
| 45 | Methyl 10-(1,8-dihydroxy-9-anthrone)-yl 3-N—cyclohexyl-carbamoylpropanoate | | H | cyclohexyl | —CH$_3$ |
| 46 | Methyl 10-(1,8-dihydroxy-9-anthrone)-yl 3-N,N—di-(2-hydroxyethyl)-carbamoylpropanoate | | —CH$_2$CH$_2$OH | —CH$_2$CH$_2$OH | —CH$_3$ |
| 47 | Methyl 10-(1,8-dihydroxy-9-anthrone)-yl 3-N—hydroxy-ethylcarbamoylpropanoate | | H | —CH$_2$—CH$_2$OH | —CH$_3$ |
| 48 | Methyl 10-(1,8-dihydroxy-9-anthrone)-yl 3-(N—2,3-dihydroxypropylcarbamoyl)-propanoate | | H | —CH$_2$—CHOH—CH$_2$OH | —CH$_3$ |
| 49 | Methyl 10-(1,8-dihydroxy-9-anthrone)-yl 3-[N—(2-ethyloxy-ethyl)]-carbamoylpropanoate | | H | —(CH$_2$)$_2$—O—(CH$_2$)$_2$OH | —CH$_3$ |
| 50 | Methyl 10-(1,8-dihydroxy-9-anthrone)-yl 3-N—morpholino-carbamoylpropanoate | | —(CH$_2$)$_2$—O—(CH$_2$)$_2$— | | —CH$_3$ |
| 51 | Methyl 10-(1,8-dihydroxy-9-anthrone)-yl 3-N—pyrrolidino- | | —(CH$_2$)$_4$— | | —CH$_3$ |

TABLE III-continued $$R_1 = \begin{array}{c} \text{CON}{<}^{R_3}_{R_4} \\ | \\ \text{CO}_2R_5 \end{array} \text{ and/or } \begin{array}{c} \text{CO}_2R_5 \\ | \\ \text{CON}{<}^{R_3}_{R_4} \end{array}$$

| Compound No. | (b) | (c) | $R_3$ | $R_4$ | $R_5$ |
|---|---|---|---|---|---|
| | carbamoylpropanoate | | | | |
| 52 | Methyl 10-(1,8-dihydroxy-9-anthrone)-yl 3-N—piperidino-carbamoylpropanoate | | | $-(CH_2)_5-$ | $-CH_3$ |
| 53 | Methyl 10-(1,8-dihydroxy-9-anthrone)-yl 3(N,N—dimethyl-carbamoyl)-propanoate | | $-CH_3$ | $-CH_3$ | $-CH_3$ |
| 54 | Ethyl 10-(1,8-dihydroxy-9-anthrone)-yl 3-[N,N—di(2-hydroxyethyl)-carbamoyl]-propanoate | | $-CH_2-CH_2OH$ | $-CH_2-CH_2OH$ | $-C_2H_5$ |
| 55 | Ethyl 10-(1,8-dihydroxy-9-anthrone)-yl 3-N—hydroxyethyl)-carbamoylpropanoate | | H | $-CH_2-CH_2OH$ | $-C_2H_5$ |
| 56 | Ethyl 10-(1,8-dihydroxy-9-anthrone)-yl 3-N,N—(dihydroxypropyl)-carbamoylpropanoate | | $-CH_2-CHOH-CH_2OH$ | $-CH_2-CHOH-CH_2OH$ | $-C_2H_5$ |
| 57 | Ethyl 10-(1,8-dihydroxy-9-anthrone)-yl 3- N(2-hydroxyethyl-oxyethyl)-carbamoylpropanoate | | H | $-(CH_2)_2-O-(CH_2)_2OH$ | $-C_2H_5$ |
| 58 | Ethyl 10-(1,8-dihydroxy-9-anthrone)-yl 3-(4-methylpiperazino)-carbamoylpropanoate | | | $-(CH_2)_2-N[CH_3]-(CH_2)_2-$ | $-C_2H_5$ |
| 59 | Ethyl 10-(1,8-dihydroxy-9-anthrone)-yl 3-(4-hydroxyethyl-piperazino)-carbamoylpropanoate | | | $-(CH_2)_2-N[(CH_2)_2OH]-(CH_2)_2-$ | $-C_2H_5$ |

Among the primary or secondary amine salts of formula IIb or IIc, there can be cited in particular the compounds collected below in Table IV:

TABLE IV

| Compound No. | | $R_3$ | $R_4$ |
|---|---|---|---|
| 60 | Ammonium 10-(1,8-dihydroxy-9-anthrone)-yl 3-carbamoylpropanoate | H | H |
| 61 | Methylammonium 10-(1,8-dihydroxy-9-anthrone)-yl 3-carbamoylpropanoate | H | $-CH_3$ |
| 62 | Ethylammonium 10-(1,8-dihydroxy-9-anthrone)-yl 3-carbamoylpropanoate | H | $-C_2H_5$ |
| 63 | Propylammonium 10-(1,8-dihydroxy-9-anthrone)-yl 3-carbamoylpropanoate | H | $-nC_3H_7$ |
| 64 | 2-hydroxyethylammonium 10-(1,8-dihydroxy-9-anthrone)-yl 3-N—(2-hydroxyethyl)-carbamoylpropanoate | H | $-CH_2-CH_2OH$ |
| 65 | di-(2-hydroxyethylammonium) 10-(1,8-dihydroxy-9-anthrone)-yl 3-N,N—di-(2-hydroxyethyl)-carbamoylpropanoate | $-CH_2-CH_2OH$ | $-CH_2-CH_2OH$ |
| 66 | 2,3-dihydroxypropylammonium 10-(1,8-dihydroxy-9-anthrone)-yl 3-N—(2,3-dihydroxypropyl)-carbamoylpropanoate | H | $-CH_2-CHOH-CH_2OH$ |
| 67 | 2-hydroxyethyloxyethylammonium 10-(1,8-dihydroxy-9-anthrone)-yl 3-N—(2-hydroxyethyloxyethyl)-carbamoylpropanoate | H | $-(CH_2)_2-O-(CH_2)_2OH$ |
| 68 | Morpholinium 10-(1,8-dihydroxy-9-anthrone)-yl-3-morpholino-propanoate | | $-(CH_2)_2-O-(CH_2)_2-$ |
| 69 | Pyrrolidinium 10-(1,8-dihydroxy-9-anthrone)-yl -3-(pyrrolidinocarbamoyl)-propanoate | | $-(CH_2)_4-$ |

Among the compounds of formula I in which the group $R_1$ represents the group (d), there can be cited in particular those collected below in Table V.

TABLE V

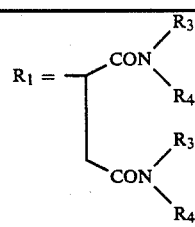

| Compound No. | $R_3$ | $R_4$ |
|---|---|---|

| 70 | 10-(1,8-dihydroxy-9-anthrone)-yl N,N'—dimethyl-disuccinamide | H | —CH$_3$ |
| 71 | 10-(1,8-dihydroxy-9-anthrone)-yl N,N'—diethyl-disuccinamide | H | —C$_2$H$_5$ |
| 72 | 10-(1,8-dihydroxy-9-anthrone)-yl N,N'—diisopropyl-disuccinamide | H | —iso C$_3$H$_7$ |
| 73 | 10-(1,8-dihydroxy-9-anthrone)-yl N,N'—dibutyl-disuccinamide | H | —nC$_4$H$_9$ |
| 74 | 10-(1,8-dihydroxy-9-anthrone)-yl N,N'—tetramethyl-disuccinamide | —CH$_3$ | —CH$_3$ |
| 75 | 10-(1,8-dihydroxy-9-anthrone)-yl N,N'—tetraethyl-disuccinamide | —C$_2$H$_5$ | C$_2$H$_5$ |

The compounds according to the invention are spaced by the Michael reaction according to the method described by O.E. Schultz and G. Frey, Arch. Pharm. 310, 781–787 (1977), consisting of reacting 1,8-dihydroxy-9-anthrone (or anthralin) in an organic solvent under an inert atmosphere, possibly in the presence of a basic catalyst, with an unsaturated compound in which the double bond is conjugated and activated by an electro-negative unsaturated group.

The reaction is, in general, carried out at the boiling temperature of the organic solvent for at least 8 hours, and 4-dimethylaminopyridine or lithium or sodium methylate are preferably utilized as basic catalyst.

When the product crystallizes within the reaction mixture when formed or on cooling, it is filtered off, washed, then dried under reduced pressure.

In the other cases, the reaction medium is concentrated under reduced pressure, and the residue is either crystallized from an appropriate solvent or purified by chromatography on silica gel.

The synthesis of the compounds according to the invention can be represented by the following reaction scheme (A):

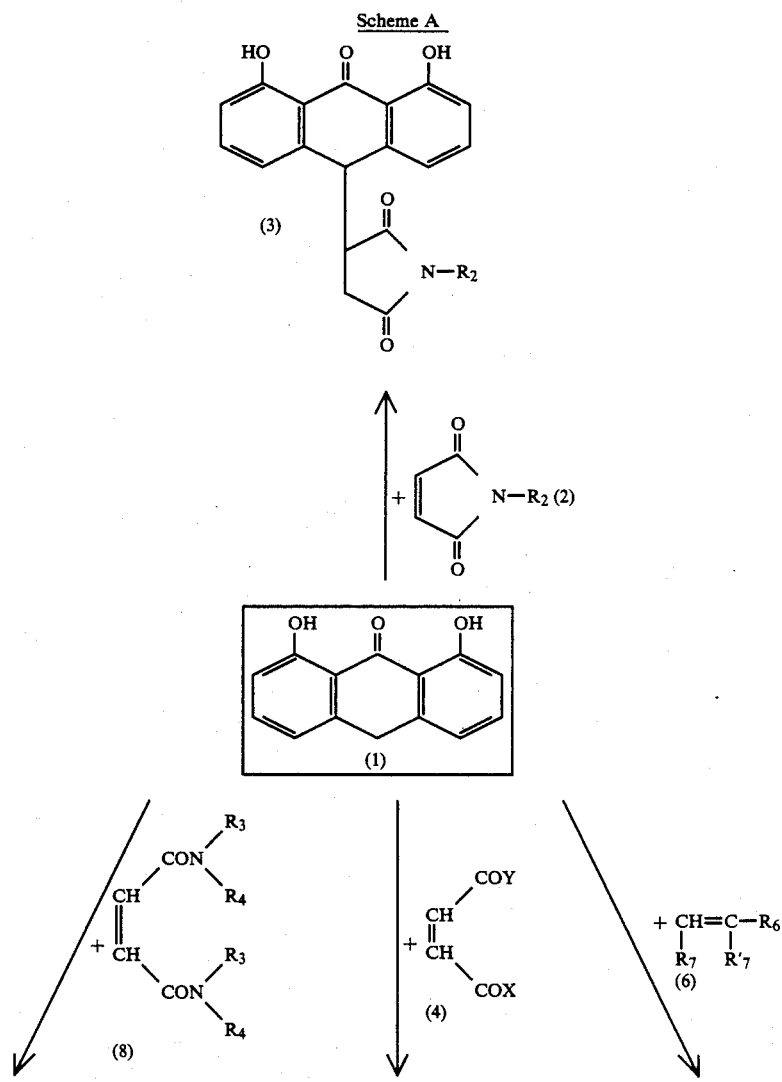

-continued
Scheme A

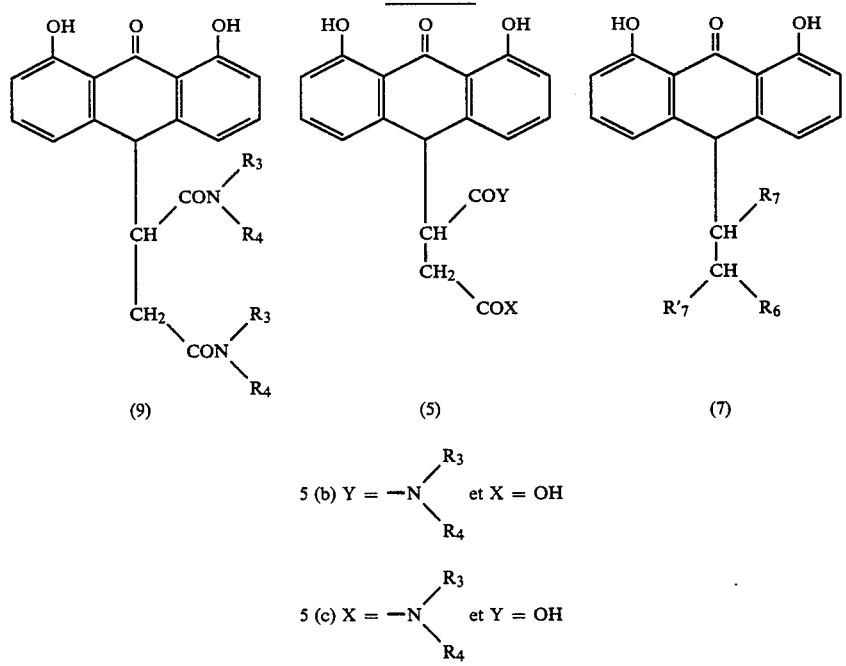

The compounds of formula (3) are obtained by reacting a molar equivalent of maleimide $R_2=H$ or an N-substituted maleimide (2) $R_2\neq H$ with anthralin (1).

The compounds of formula (5b or 5c) are obtained by reacting maleamic acid (4) $X=OH$ and $Y=-NH_2$, or an N-substituted derivative or maleamic acid (4) $X=OH$ and $Y=NR_3R_4$ with $R_3=H$ and $R_4\neq H$, or a N,N-disubstituted derivative of maleamic acid (4) $X=OH$ and $Y=NR_3R_4$ with $R_3=R_4\neq H$ with anthralin (1).

The compounds of formula (7) are obtained by reacting an unsaturated compound of formula (6), preferably in excess, with anthralin (1).

Finally, the compounds of formula (9) are obtained by reacting a dimealamide (8) with anthralin (1).

The compounds of formula (5b) or (5c) can likewise be obtained according to another method, as in the following reaction scheme (B):

Scheme B

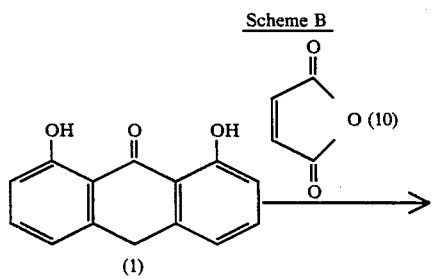

-continued
Scheme B

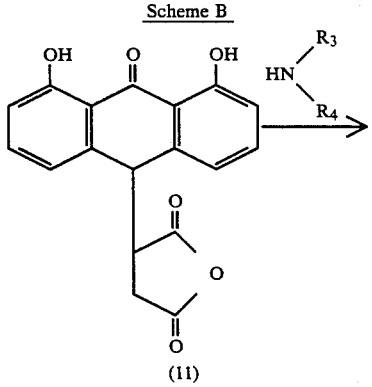

-continued
Scheme B

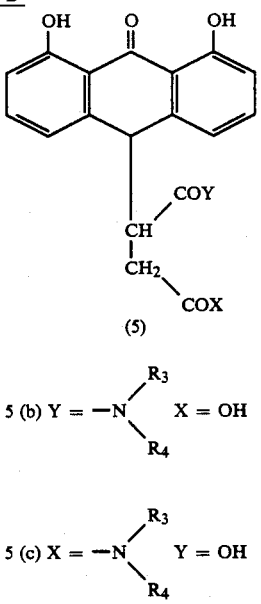

5 (b) Y = —N(R₃)(R₄)  X = OH 5 (c) X = —N(R₃)(R₄)  Y = OH

This process consists of first preparing the 10-(1,8-dihydroxy-9-anthrone)-yl succinic anhydride of formula (11) according to the procedure described by O.E. Schultz and G. Frey (Arch. Pharm. 310, 766–780 (1977)) by a Michael reaction between anthralin (1) on the one hand and maleic anhydride (10) on the other.

It is possible to obtain from the intermediate compound (11) compounds of formula (5b) or (5c) by reacting it with a molar equivalent of primary or secondary amine at a temperature comprised between −10° and 50° C.

The salts of formula (IIb) and IIc) can also be obtained starting with the intermediate compounds (11) by reacting under the same conditions two equivalents of the corresponding primary amine or secondary amine with the anhydride.

The salts of formula (IIb) and (IIc) can furthermore be obtained from compounds of formula (5b) or (5c) by washing with hydrochloric acid.

The compounds of formula (5) obtained by a Michael reaction according to reaction scheme (A) or reaction scheme (B) can exist in the form of a mixture of isomers, i.e., of compounds of formula 5b and 5c, to the degree that the reaction cannot always be directed with certainty.

Finally, it must be marked that the compounds according to the invention, with the exception of the compounds in which $R_7 = R'_7 = H$, all possess at least one asymmetric carbon atom, such that they can likewise exist in the form of their optical isomers (d and l) or of a mixture of these isomers.

The unsaturated starting compounds for the preparation of the compounds according to the invention are mainly commercially available or can be obtained by known methods which are described in the literature. Thus, N-hydroxymethyl-maleimide can be prepared by the action of formaldehyde on maleimide according to the method described by: P.O. Tawney, et al., JOC, p. 15 (1961).

N-carbamoylmaleimide can be prepared according to the method described by P.O. Tawney, et al., JOC, Vol. 25, p. 56 (1960); the dimaleimides are prepared according to the method described by M. Roth, Helv. Chim. Act. 62, p. 1966 (1979).

The N-substituted maleamic acids are likewise prepared by opening of maleic anhydride by a primary or secondary amine, according to the method described by Y. Liwschitz, et al., JACS, 78, 3069 (1956).

The object of the pesent invention is likewise the utilization of the compounds according to the invention in human or veterinary medicine, in particular in the treatment of psoriasis and/or warts, and in cosmetics.

Cutaneous psoriasis is essentially manifested by the appearance of dry, whitish, or nacreous scales.

Psoriasis preferentially manifests on the knees and elbows, on the sacrum, on the soles of the feet, the palms of the hands, the face, and likewise on hairy hide.

The trials carried out enabled showing that these compounds have good activity when incorporated in various pharmaceutical vehicles intended for utilization by the systemic route and, in particular, percutaneously.

Several examples of preparation of the compounds according to the present invention will now be given, by way of illustration and without any limitative nature.

EXAMPLE I

Preparation of 10-(1,8-dihydroxy-9-anthrone)-y1-succinimide (No. 1):

To an agitated solution of 1.12 g of anthralin (5 mmol) in 40 ml of chloroform, there are added, in one addition, 0.48 g of maleimide (1 eg.) and also several crystals of 4-dimethylamino pyridine, with protection from light and under an inert atmosphere.

The reaction mixture is then kept at the boiling point of chloroform for about 7 hours. A yellow solid crystallizes during the reaction. After the end of the reaction, followed by thin layer silica gel chromatography, the reaction medium is left to return to ambient temperature.

The solid is then filtered off, dried under reduced pressure, and gives 1.3 g of 10-(1,8-dihydroxy-9-anthrone)-y1succinimide, pale yellow in color, having a decomposition point of 220° C.

| Analysis: $C_{18}H_{13}NO_5$ | | | | |
|---|---|---|---|---|
| Calc. | C: 66.87 | H: 4.05 | N: 4.33 | O: 24.74 |
| Found: | 66.85 | 4.15 | 4.43 | 24.65 |

EXAMPLE 2

Preparation of 10-(1,8-dihydroxy-9-anthrone)-y1-N-hydroxymethyl succinimide (No. 3):

According to the same procedure as described in Example 1 above, 1.12 g of anthralin are reacted in chloroform in the presence of 0.63 g of N-hydroxymethyl maleimide (1 eq.) in the presence of several crystals of DMAP.

After the end of the reaction a yellow solid, decomposing at 200° C., is isolated from the reaction mixture.

| Analysis: $C_{19}H_{15}NO_6$ | | | |
|---|---|---|---|
| Calc. | C: 64.58 | H: 4.28 | N: 3.96 |
| Found: | 65.01 | 4.32 | 4.00 |

EXAMPLE 3

Preparation of 10-(1,8-dihydroxy-9-anthrone)-yl-N-ethyl succinimide (No. 5):

Under a nitrogen atmosphere and protected from atmosphere moisture and from light, a solution of 4.5 g of anthralin with 1.1 equivalent of N-ethyl maleimide and 20 mg of 4-dimethylamino-pyridine in 100 ml of chloroform is kept at the boiling point of chloroform for fifteen hours.

The reaction mixture, after cooling, is deposited directly onto a silica gel column. The expected product is elute with ethyl acetate. After evaporation of the elution phases, there are obtained 6.5 g of bright yellow crystals having a melting point of 200° C.

| Analysis: $C_{10}H_{17}NO_5$ | | | | |
|---|---|---|---|---|
| Calc. | C: 68.37 | H: 4.88 | N: 3.99 | O: 22.77 |
| Found: | 68.49 | 4.94 | 4.03 | 22.87 |

EXAMPLE 4

Preparation of 10-(1,8-dihydroxy-9-anthrone)-yl-N-carbamoylsuccinimide (No. 8):

An agitated mixture of 1.1 g of anthralin and one equivalent of N-carbamoyl maleimide in 20 ml of anhydrous acetonitrile, placed under an inert atmosphere and protected from atmospheric moisture and light, is kept at the reflux of acetonitrile for 8 hours.

After cooling, the solid is drained, washed with acetonitrile, then dried under reduced pressure over phosphorus pentoxide. There are thus obtained 1.45 g of yellow crystals having an instantaneous melting point of 200° C.

| Analysis: $C_{19}H_{14}N_2O_6$ | | | | |
|---|---|---|---|---|
| Calc. | C: 62.29 | H: 3.85 | N: 7.65 | O: 26.21 |
| Found: | 62.17 | 3.93 | 7.70 | 26.22 |

EXAMPLE 5

Preparation of 10-(1,8-dihydroxy-9-anthrone)-yl-N-phenyl succinimide (No. 9):

An agitated mixture of 4.5 g of anthralin and an equivalent of N-phenyl maleimide in 100 ml of acetonitrile placed under an inert atmosphere and protected from atmospheric moisture and from light is kept at the reflux of acetonitrile for 17 hours. After cooling, the solid is drained, washed with chloroform, then with benzene; after drying at 120° C. under reduced pressure, 7 g of a bright yellow solid are obtained, with an instaneous melting point of 260° C.

| Analysis: $C_{24}H_{17}NO_5$ | | | | |
|---|---|---|---|---|
| Calc. | C: 72.17 | H: 4.29 | N: 3.51 | O: 20.03 |
| Found: | 72.03 | 4.25 | 3.47 | 20.00 |

EXAMPLE 6

Preparation of 10-(1,8-dihydroxy-9-anthrone)-yl-propanoic ethyl ester (No. 10):

A mixture of 4.52 g of anthralin (0.02 mol), 6 ml of ethyl acrylate and 1 ml of 0.5% lithium methylate, in 35 ml of anhydrous chloroform is kept at the boiling point of the solvent for 5 hours, protected from light under an inert atmosphere. After the mixture has been left at ambient temperature for about 48 hours, silica gel chromatography is carried out.

The ethyl 10-(1,8-dihydroxy-9-anthrone)-yl propanoate is then eluted with a benzene-chloroform mixture (50/50), then recrystallized from hexane. This compound occurs in the form of a yellow solid with a melting point of 90° C.

| Analysis: $C_{19}H_{18}O_5$ | | | |
|---|---|---|---|
| Calc. | C: 69.93 | H: 5.55 | O: 24.51 |
| Found: | 69.83 | 5.54 | 24.50 |

EXAMPLE 7

Preparation of 10-(1,8-dihydroxy-9-anthrone)-yl-propanoic ester (No. 11):

A solution of 6 g of ethyl 10-(1,8-dihydroxy-9-anthrone)-yl propanoate in a mixture of 150 ml of dioxane and 150 ml of 5N hydrochloric acid is kept under an inert atmosphere and protected from light for 2 hours at 100° C.

The reaction mixture is then concentrated under reduced pressure.

The residue is deposed on a silica gel chromatography column and the expected acid is eluted with a 1:1 benzene/ethyl acetate mixture, then recrystallized from toluene. There is obtained 1 g of yellow powder with a melting point of 191° C. The mass spectrum gives the expected parent peak at m/e=298 ($C_{17}H_{14}O_5$).

EXAMPLE 8

Preparation of 10-(1,8-dihydroxy-9-anthrone)-yl succinamic acid (No. 19):

(a) To a solution of 0.678 g of anthralin (3 x 10⁻³ mol) in 25 ml anhydrous acetonitrile under an inert atmosphere and protected from light and atmospheric moisture, there is added 0.345 g (1 eq.) of maleamic acid, in one portion. The reaction mixture is then kept at the boiling point of the solvent for 6 hours. 10-(1,8-dihydroxy-9-anthrone)-yl succinamic acid crystallizes within the reaction mixture as it forms.

At the end of the reaction, as followed by thin layer chromatography, the mixture is kept at ambient temperature; the pale yellow solid is then filtered off, and is dried under reduced pressure.

There are thus obtained 0.85 g of the expected product, which decomposes at 220° C.

| Analysis: $C_{18}H_{15}NO_6$ | | | | |
|---|---|---|---|---|
| Calc. | C: 63.34 | H: 4.43 | N: 4.10 | O: 28.13 |
| Found: | 63.46 | 4.44 | 4.09 | 28.12 |

(b) To a solution of 0.972 g (3 x 10⁻³ mol) of 10-(1,8-dihydroxy-9-anthrone)-yl succinic anhydride (prepared according to O.E Schultz and G. Frey, Arch. Pharm. 310, 776–780, 1977) in 80 ml of acetonitrile, agitated at 5° C. under an inert atmosphere and protected from light, there is added dropwise a solution of ammonia (1 eq.) diluted with 20 ml of acetonitrile. The 10-(1,8-dihydroxy-9-anthrone)-yl succinamic acid precipitates as it is formed. It is drained, then washed with a solution of hydrochloric acid in ether and then dried under reduced pressure. There is thus otained 0.9 g of a yellow product which decomposes at 220° C.

EXAMPLE 9

Preparation of 10-(1,8-dihydroxy-9-anthrone)-yl N-methyl succinamic acid (No. 20):

An agitated mixture of 4.5 g of anthralin, one equivalent of N-ethyl maleamic acid, and 20 mg of 4-dimethylamino pyridine in 50 ml of chloroform is refluxed for 24 hours under an inert atmosphere and protected from light and atmospheric moisture.

After cooling, the yellow solid formed is drained, washed with chloroform, then with a dilute aqueous acetic acid solution, and is then agitated for a long time in water. The solid is again filtered off, then dried over phosphorus pentoxide under reduced pressure. There is thus obtained 1.5 g of yellow crystals with a melting point (decomposition) of 260° C.

| Analysis: $C_{19}H_{17}NO_6$ | | | | |
|---|---|---|---|---|
| Calc. | C: 64.22 | H: 4.82 | N: 3.94 | O: 27.02 |
| Found: | 64.07 | 4.79 | 3.85 | 26.93 |

EXAMPLE 10

Preparation of 10-(1,8-dihydroxy-9-anthrone)-yl N-ethyl succinamic acid (No. 21):

An agitated mixture of 4.5 g of anthralin with an equivalent of N-ethyl maleamic acid and several crystals of DMAP in 50 ml of chloroform is kept at the boiling point of this solvent under agitation and protected from atmospheric moisture and from light, for 8 hours. The mixture is then allowed to come to ambient temperature. The crystals are then filtered off, and are deposited, in chloroform solution, on a silica gel column.

The expected product, contaminated with an impurity, is eluted with ethyl acetate. After concentration of the elution phases, the mixture is taken up in acetone, and the impurity is eliminated by filtration. After concentration of the filtrate, there is obtained 10-(1,8-dihydroxy-9-anthrone)-yl N-ethyl succinamic acid of yellow color, melting at 190° C.

| Analysis: $C_{20}H_{19}NO_6$ | | | | |
|---|---|---|---|---|
| Calc.: | C: 65.03 | H: 5.18 | N: 3.79 | O: 25.99 |
| Found: | 65.13 | 5.12 | 3.78 | 25.91 |

EXAMPLE 11

Preparation of 10-(1,8-dihydroxy-9-anthrone)-yl N-isopropyl succinamic acid (No. 23):

An agitated mixture of 4.5 g of anthralin, an equivalent of N-isopropyl succinamic acid, and 20 mg of 4-dimethyl-aminopyridine in 50 ml of chloroform is refluxed for 24 hours. The reaction mixture is protected from atmospheric moisture and light. After cooling, the precipitate formed is drained, washed with chloroform and then with dilute acetic acid, and is finally dried at 120° C. at reduced pressure over phosphorus pentoxide. There are obtained 3.2 g of yellow crystals with an instantaneous melting point of 220° C.

| Analysis: $C_{21}H_{21}NO_6$ | | | | |
|---|---|---|---|---|
| Calc.: | C: 65.78 | H: 5.52 | N: 3.65 | O: 25.04 |
| Found: | 65.77 | 5.55 | 3.54 | 24.86 |

EXAMPLE 12

Preparation of 10-(1,8-dihydroxy-9-anthrone)-yl N-(2-hydroxyethyl) succinamic acid (No. 27):

At ambient temperature, under an inert atmosphere and protected from light, a mixture is agitated of 0.486 g (1.5 mmol) of 10-(1,8-dihydroxy-9-anthrone)-yl succinic anhydride and an equivalent of ethanolamine in 50 ml of anhydrous chloroform.

After agitation for 48 hours, a white powder is filtered off and is then treated with a 0.1 N solution of hydrochloric acid at 0° C. The 10-(1,8-dihydroxy-9-anthrone)-yl N-(2-hydroxyethyl) succinamic acid is then drained and dried under reduced pressure.

| Analysis: $C_{20}H_{19}NO_7$ | | | | |
|---|---|---|---|---|
| Calc.: | C: 62.33 | H: 4.97 | N: 3.63 | O: 29.06 |
| Found: | 62.45 | 5.00 | 3.72 | 29.04 |

EXAMPLE 13

Preparation of 10-(1,8-dihydroxy-9-anthrone)-yl morpholinosuccinamic acid (No. 29):

A suspension of 600 mg of the salt of Example 23 below in 10 ml of 5N hydroxhloric acid is agitated for about half an hour. The solid is filtered off, then rapidly washed with acetone. There are thus obtained 300 mg of yellow powder after drying, with a melting point (instantaneous) of 150° C.

| Analysis: $C_{22}H_{21}NO_7$ | | | | |
|---|---|---|---|---|
| Calc.: | C: 64.23 | H: 5.14 | N: 3.40 | O: 27.22 |
| Found: | 64.14 | 5.20 | 3.34 | 27.34 |

EXAMPLE 14

Preparation of 10-(1,8-dihydroxy-9-anthrone)-yl pyrrolidino succinamic acid (No. 30):

A suspension of 1 g of the salt of Example 24 below is agitated in 10 ml of 5N hydrochloric acid at 0° C. under an inert atmosphere for half an hour. The solid is then drained, rapidly washed with acetone, and then dried. 0.5 of yellow powder is obtained, with an instanteous melting point of 215° C.

| Analysis: $C_{22}H_{21}NO_6$ | | | | |
|---|---|---|---|---|
| Calc.: | C: 66.83 | H: 5.35 | N: 3.54 | O: 24.28 |
| Found: | 66.87 | 5.34 | 3.59 | 24.48 |

EXAMPLE 15

Preparation of 10-(1,8-dihydroxy-9-anthrone)-yl 4-methylpiperazino succinamic acid (No. 32):

To a solution of 1.35 g of anthralin (6 mmol) in 180 ml of chloroform placed under an inert atmosphere, there are added, with protection from light, 1.2 g of 4-methylpiperazino maleamic acid. This mixture is agitated and brought to the boiling temperature of the solvent during 18 hours. The expected product crystallizes from the solution as it forms.

After cooling, it is drained, then dried under reduced pressure at 120° C. There are thus obtained 1.32 g of 10-(1,8-dihydroxy-9-anthrone)-yl 4-methylpiperazino succinamic acid, in the form of a pale yellow powder which decomposes at 210° C.

| Analysis: $C_{23}H_{24}N_2O_6$ | | | |
|---|---|---|---|
| Calc.: | C: 65.08 | H: 5.70 | N: 6.60 | O: 22.62 |
| Found: | 64.35 | 5.79 | 6.54 | 23.09 |

EXAMPLE 16

Preparation of 10-(1,8-dihydroxy-9-anthrone)-yl 4-(2-hydroxyethyl)piperazino succinamic acid (No. 33):

To a solution of 0.972 g (3mmol) of 10-(1,8-dihydroxy-9-anthrone)-yl succinic anhydride in 50 ml of chloroform agitated at ambient temperature in an inert atmosphere and exclusion of light, one adds in small fractions an equivalent of 4-(2-hydroxyethyl)piperazine (0.390 g=10 mmol). The reaction mixture is then permitted to stand overnight at ambient temperature. The reaction mixture is then collected and dried under reduced pressure at 120° C.

The product is obtained in the form of a yellow-brown solid decomposing at about 190° C.

| Analysis: $C_{24}H_{26}N_2O_7$ (monohydrate) | | | |
|---|---|---|---|
| Calc.: | C: 61.01 | H: 5.97 | N: 5.93 | O: 27.09 |
| Found: | 61.41 | 5.83 | 6.24 | 26.69 |

EXAMPLE 17

Preparation of 10-(1,8-dihydroxy-9-anthrone)-yl N,N-di(2-hydroxyethyl)-succinamic acid (No. 38):

To a solution of 0.972 g (3 mmol) of 10-(1,8-dihydroxy-9-anthrone)-yl succinamic acid in 60 ml of acetonitrile, agitated at ambient temperature and under a nitrogen atmosphere, there is slowly added, with protection from light, an equivalent of diethanolamine diluted with 20 ml of acetonitrile. The reaction mixture is then left overnight at ambient temperature.

After the insoluble matter has been removed by filtration, the filtrate is concentrated under reduced pressure. After washing with ether, draining and drying under reduced pressure, a product is obtained which decomposes at about 100° C.

| Analysis: $C_{22}H_{23}NO_8$ | | | |
|---|---|---|---|
| Calc.: | C: 59.05 | H: 5.63 | N: 3.13 |
| Found: | 59.05 | 5.47 | 3.20 |

EXAMPLE 18

Preparation of Methyl 10-(1,8-dihydroxy-9-anthrone)-yl 3-carbamoylpropanoate (No. 40):

To an agitated solution of 1 g of 10-(1,8-dihydroxy-9-anthrone)-yl succinamic acid in 150 ml of methanol, cooled to 0° C., there is added an excess of diazomethane dissolved in ether.

The mixture is kept overnight at ambient temperature. The next day, after 2 ml of acetic acid have been added to destroy the excess of diazomethane, the reaction medium is concentrated at reduced pressure. The residue obtained is dissolved in the minimum of chloroform, then deposited on a silica gel column. The expected ester is eluted with acetone. After concentration of the acetone, a yellow powder is obtained having a melting point of 250° C.

| Analysis: $C_{19}H_{17}NO_6$ | | | |
|---|---|---|---|
| Calc.: | C: 64.22 | H: 4.82 | N: 3.94 | O: 27.01 |
| Found: | 64.18 | 4.84 | 3.84 | 26.87 |

EXAMPLE 19

Preparation of Methyl 10-(1,8-didhydroxy-9-anthrone)-yl N-morpholine-3-carbamoylpropanoate (No. 50):

A solution of 0.5 g of 10-(1,8-dihydroxy-9-anthrone)-yl morpholinosuccinamic acid in 30 ml of anhydrous methanol, two drops of sulfuric acid, and 1 ml of 2,2-dimethoxypropane is refluxed for 10 hours under an argon atmosphere and protected from atmospheric moisture and light. The reaction mixture is filtered, and the filtrate is concentrated under reduced pressure; the residue is directly taken up in the minimum of benzene. The benzene phase is deposited on a silica gel chromatography column. The expected product is eluted with a benzeneacetone (1:1) mixture. After concentration of the elution phases and drying, 0.30 g of yellow powder are obtained, with a melting point of 158° C.

| Analysis: $C_{23}H_{23}NO_7$ | | | |
|---|---|---|---|
| Calc.: | C: 64.93 | H: 5.45 | N: 3.29 | O: 26.32 |
| Found: | 64.94 | 5.46 | 3.28 | 26.28 |

EXAMPLE 20

Preparation of 2-hydroxyethylammonium 10-(1,8-dihydroxy-9-anthrone)-yl N-(2-hydroxyethyl)-3-carbamoylpropanoate (No. 64):

To a solution of 0.366 g of ethanolamine (6 mmol) in 50 ml of chloroform, agitated at ambient temperature, there are added in small fractions 0.972 g (3 mmol) of 10-(1,8-dihydroxy-9-anthrone)-yl-succinic anhydride. The reaction medium, after being homogenized, gives rise to crystals of a pale yellow color.

After one night, the crystals are filtered off and dried. The salt thus isolated (1.25 g) is in the form of a pale yellow powder which decomposes at about 170° C.

| Analysis: $C_{22}H_{26}N_2O_8$ | | | |
|---|---|---|---|
| Calc.: | C: 59.18 | H: 5.87 | N: 6.27 | O: 28.67 |
| Found: | 59.31 | 5.77 | 6.20 | 28.67 |

EXAMPLE 21

Preparation of di(2-hydroxyethyl)ammonium 10-(1,8-dihydroxy-9-anthrone)-yl-N,N-di(2-hydroxyethyl)-3(No. 65):

0.972 g of 10-(1,8-dihydroxy-9-anthrone)-yl succinic anhydride is dissolved in 120 ml of hot, anhydrous acetonitrile. The solution obtained, after filtration, is cooled to 0° C., and there are then added dropwise, with agitation, two equivalents of diethanolamine diluted with 80 ml of acetonitrile.

The expected salt progressively crystallizes; agitation is continued for about 2 hours after the end of addition. After filtering off the solid and drying it under reduced pressure, there are obtained 1.5 g of a product in the form of pale yellow crystals with glints of green, decomposing at about 150° C.

| Analysis: $C_{26}H_{34}N_2O_{10}$ | | | | |
|---|---|---|---|---|
| Calc.: | C: 58.41 | H: 6.41 | N: 5.24 | O: 29.93 |
| Found: | 58.52 | 6.38 | 5.23 | 29.92 |

EXAMPLE 22

Preparation of 2-hydroxyethyloxyethyl 10-(1,8-dihydroxy-9-anthrone)-yl N-(2-hydroxyethyloxyethyl)-3-carbamoylpropanoate (No. 67):

Under a nitrogen atmosphere, protected from light, and at ambient temperature, a mixture is agitated of 0.972 g (3 mmol) of 10-(1,8-dihydroxy-9-anthrone)-yl succinic anhydride and 0.631 g (6 mmol) of 2-hydroxyethyloxyethylamine in 50 ml of chloroform. The medium becomes progressively homogenous and the amine salt then slowly crystallizes. After one night, the solid is filtered off, then dried under reduced pressure. 1.1 g of product are thus obtained in the form of a beige powder which decomposes at about 150° C.

| Analysis: $C_{26}H_{34}N_2O_{10}$ | | | | |
|---|---|---|---|---|
| Calc.: | C: 58.41 | H: 6.41 | N: 5.24 | O: 29.93 |
| Found: | 58.31 | 6.38 | 5.28 | 30.13 |

EXAMPLE 23

Preparation of morpholinium 10-(1,8-dihydroxy-9-anthrone)-yl morpholino-3-carbamoylpropanoate (No. 68):

To an agitated suspension of 1 g of 10(1,8-dihydroxy-9-anthrone)-yl succinic anhydride in 100 ml of chloroform, cooled to 0° C. and placed under an inert atmosphere with protection from light, there are added dropwise two equivalents of morpholine. At the end of addition, the solution obtained is filtered. The filtrate is concentrated under reduced pressure.

The solid obtained is dissolved in ether, filtered and then dried under reduced pressure. 1.1 g of beige powder are thus obtained, with an instantaneous melting point of 130° C. This hygroscopic product is analyzed in the form of the hemihydrate.

| Analysis: $C_{26}H_{30}N_2O_8 \cdot \frac{1}{2}H_2O$ | | | | |
|---|---|---|---|---|
| Calc.: | C: 61.54 | H: 6.11 | N: 5.52 | O: 26.82 |
| Found: | 61.79 | 5.90 | 4.93 | 26.98 |

EXAMPLE 24

Preparation of pyrrolidinium 10-(1,8-dihydroxy-9-anthrone)-yl pyrrolidino-3-carbamoylpropanoate (No. 69):

To an agitated suspension of 0° C. of 3.24 g of 10-(1,8-dihydroxy-9-anthrone)-yl succinic anhydride in 150 ml of chloroform, protected from light and from atmospheric moisture under an inert atmosphere, there are slowly added two equivalents of pyrrolidine. After two hours of agitation, the chloroform solution is concentrated under reduced pressure, and the residue is solidified in anhydrous ether. The brown solid thus obtained is filtered off, again washed with ether, then dried under reduced pressure. This brown powder melts at 120° C.; it is very hygroscopic, and is analyzed in the form of the monohydrate.

| Analysis: $C_{26}H_{30}N_2O_6 \cdot 1\,H_2O$ | | | | |
|---|---|---|---|---|
| Calc.: | C: 64.45 | H: 6.65 | N: 5.78 | O: 23.11 |
| Found: | 63.93 | 6.70 | 5.83 | 23.40 |

EXAMPLE 25

Preparation of 10-(1,8-dihydroxy-9-anthrone)-yl-N,N'-diisopropyl disuccinamide (No. 72);

An agitated mixture 1 g of anthralin and 1 g of N,N' diisopropyl dimaleimide in 50 ml of ahydrous acetonitrile is refluxed for 5 hours, protected from atomspheric moisture and from light.

After cooling, the solid is filtered off, washed with acetonitrile, then dried under reduced pressure. There are obtained 1.72 g of pale yellow cyrstals which decompose at 280° C.

| Analysis: $C_{24}H_{28}N_2O_5$ | | | | |
|---|---|---|---|---|
| Calc.: | C: 67.90 | H: 6.65 | N: 6.60 | O: 18.85 |
| Found: | 67.87 | 6.58 | 6.45 | 18.68 |

Regarding the treatment of psoriasis or warts, a composition containing a compound of the present invention is topically administered directly to the affected area. It may, for example, be applied as part of a thickened lotion. A suitable thickening agent for such an application would be petroleum jelly.

An example of an anti-psoriasis composition embodied within the scope of the present invention is as follows:

10-(1,8-dihydroxy-9-anthrone)-yl
N-carbamoyl succinimide; 1.5 g
Salicylic acid; 0.7 g
Petroleum jelly; 100 g To the petroleum jelly at 60° C., it is added under stirring the active ingredient and then the salicylic acid. After cooling to ambient temperatures, the suspension obtained is refined by passing it to a roller mill.

By applying the suspension once a day during three weeks, excellent results are otained on the psoriasis areas very similar to those obtained with anthraline but with no primary irritation and without staining of the skin.

We claim:

1. A compound of the formula

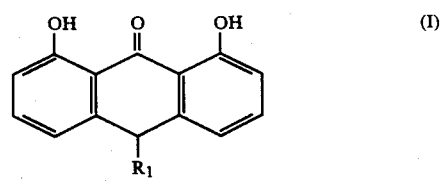

(I)

2. A compound of claim 1 in the form of an optical isomer thereof.
wherein $R_1$ is

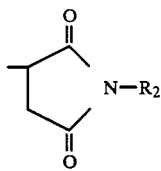

and R$_2$ is selected from the group consisting of hydrogen, straight or branched chain alky of 1–8 carbon atoms, straight or branched chain mono- or polyhydroxyalkyl having 1–3 carbon atoms, carbamoyl and phenyl.

3. The compound of claim 1 wherein the alkyl radical having 1–8 carbon atoms is selected from the group consisting of methyl, ethyl, propyl, isopropyl, butyl, isobutyl, tert-butyl, hexyl and octyl.

4. The compound of claim 1 wherein the mono-or polyhydroxyalkyl radical having 1–3 carbon atoms is selected from the group consisting of hydroxymethyl, 2-hydroxyethyl 5. The compound of claim 1 wherein the cycloalkyl consisting of cyclopropyl, cyclobutyl, cyclopentyl and cyclohexyl.

* * * * *